United States Patent [19]

Okada et al.

[11] Patent Number: 4,491,926
[45] Date of Patent: Jan. 1, 1985

[54] PARTICLE SIZE DISTRIBUTION ANALYZER

[75] Inventors: Tokuhiro Okada, Hyogoken; Masayoshi Hayashi, Kobe, both of Japan

[73] Assignee: Toa Medical Electronics Co. Ltd., Kobe, Japan

[21] Appl. No.: 353,839

[22] Filed: Mar. 1, 1982

[30] Foreign Application Priority Data

Apr. 30, 1981 [JP] Japan ................................. 56-66385

[51] Int. Cl.³ ............................................ G01N 15/00
[52] U.S. Cl. .................................... 364/555; 364/416; 377/11; 324/71.4
[58] Field of Search .................. 364/555, 416; 377/11; 324/71.4

[56] References Cited

U.S. PATENT DOCUMENTS

| | | | |
|---|---|---|---|
| 3,935,562 | 1/1976 | Stephens | 377/11 X |
| 3,936,666 | 2/1976 | Hogg et al. | 364/555 X |
| 3,936,740 | 2/1976 | Hogg et al. | 364/555 X |
| 3,982,183 | 9/1976 | Collineau et al. | 377/11 |
| 4,063,309 | 12/1977 | Hennessy et al. | 364/555 |
| 4,314,346 | 2/1982 | Feier et al. | 364/555 |
| 4,412,175 | 10/1983 | Maynarez | 364/555 X |

*Primary Examiner*—Edward J. Wise
*Attorney, Agent, or Firm*—Lucas & Just

[57] ABSTRACT

A particle size distribution analyzer includes a detector adapted to detect particles by electrical or optical differences from a medium containing the particles in dispersion and generate signals proportionally to the sizes of the detected particles, a threshold circuit adapted to remove noises or fragmental signals from the detected signals so as to obtain pulse widths at a constant position, a gate circuit adapted to decide the passage or non-passage of the particles through the threshold circuit, a counter circuit adapted to count the number of the particles fed from the gate circuit, a memory connected to the counter circuit, an arithmetic circuit connected to the memory and the detector, a controller circuit connected to the gate circuit, the memory and the counter circuit, and means for displaying or recording the data stored in the memory.

1 Claim, 6 Drawing Figures

PARTICLE SIZE DISTRIBUTION ANALYZER

BACKGROUND OF THE INVENTION

The present invention relates to a particle size distribution analyzer adapted for use in observing the health condition of microscopic particles, such as blood cells. More particularly, the invention relates to a particle size distribution analyzer adapted for use in examining a possible symptom of abnormality or disease of particles through electrical or optical differences between the particles and a medium, such as physiological salt solution, in which the particles are dispersed, wherein the dispersion medium is passed through a detection pore. The analysis is carried out by examining the pulse intervals and the pulse widths obtained in response to the particles passing through the detection pore.

It is known in the art that microscopic particles (hereinafter referred to merely as particles) are detected by their electrical or optical differences from the dispersion medium when the medium is passed through a pore in the detector. In such analytical processes it is essential to detect particles individually when they pass through the pore. In the known processes, however, it often happens that two or more particles simultaneously pass, or that several particles pass in linking states. It also happens that the particles become aggregate in places in the dispersion medium. Owing to these phenomena the intervals of generating pulses become irregular, which will result in misled data. Accordingly, to remedy this situation a special process is additionally required. The common practice is to sample an optional part of the signals, and record them in a high-speed digital recorder. Then, each recorded signal is called and displayed as a motionless waveform on an oscilloscope, from which waveforms data are read out by the use of a scale. Alternatively, a computer capable of arithmetic operation at a high speed is employed to analyze the signals directly.

However, these remedying methods have disadvantages; in the former method the range of obtaining data is considerably limited, and as a result, the obtained data can be deficient in facts or fail to reveal the truth. In addition, such after-treatment is time- and labor-consuming. In the latter method the pulse intervals range from a few microseconds to a few thousands of microseconds, so that the computer must be, for arithmetic operation, adapted for a few microseconds in such a vast range. A disadvantage is that much time is wasted in waiting from adaptation to adaptation, and that after all on average it covers only a few hundreds of microseconds.

OBJECTS AND SUMMARY OF THE INVENTION

The present invention aims at solving the problems pointed out above with respect to the known analyzing methods, and has for its object to provide an improved particle size distribution analyzer capable of examining the health condition or any other symptoms of individual particles, such as blood cells, without the use of an expensive high-speed computer.

Another object of the present invention is to provide an improved particle size distribution analyzer of economical, compact size, the analyzer being capable of operating at ease.

A further object of the present invention is to provide an improved particle size distribution analyzer capable of readily incorporation in a blood analyzer so as to impart versatility and checking ability thereto, thereby enabling the blood analyzer to find wide application.

Other objects and advantages of the present invention will become more apparent from the following description when taken in connection with the accompanying drawings which show an embodiment of the particle size distribution analyzer for the purpose of illustration only.

According to one advantageous aspect of the present invention, the particle size distribution analyzer includes a detector adapted to detect particles by electrical or optical differences from a medium containing the particles in dispersion and generate signals proportionally to the sizes of the detected particles, a threshold circuit adapted to remove noises or fragmental signals from the detected signals so as to obtain pulse widths at a constant position, a gate circuit adapted to decide the passage or non-passage of the particles through the threshold circuit, a counter circuit adapted to count the number of the particles fed from the gate circuit, a memory connected to the counter circuit, an arithmetic circuit connected to the memory and the detector, a controller circuit connected to the gate circuit, the memory and the counter circuit, and means for displaying or recording the data stored in the memory.

DETAILED DESCRIPTION OF THE INVENTION

Figure 1:
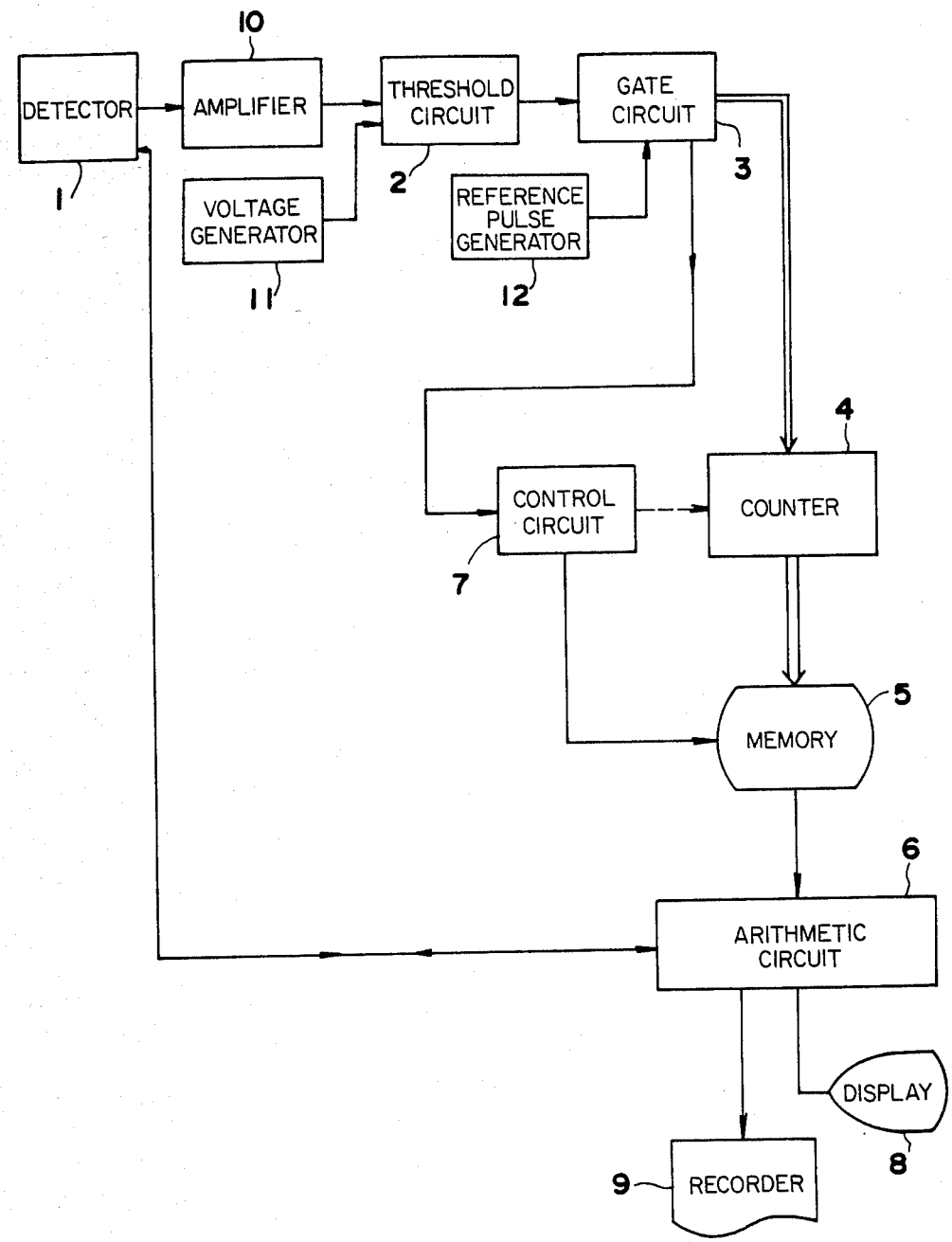
FIG. 1 is a block diagram showing one example of the embodiment according to the present invention.

Referring to FIG. 1 a detector 1 generates signals in proportion to the sizes of the particles which are detected by electrical or optical differences from the dispersion medium in which the particles are dispersed, wherein the medium is passed through a pore as it contains the particles. The detector 1 is connected to a threshold circuit 2 through an amplifier 10, the threshold circuit being adapted to remove fragmental signals or noises from the signals generated by the detector 1 so as to obtain pulse widths at a constant position. A gate circuit 3 is adapted to decide the passage or non-passage of the particles through the threshold circuit 2. A counter circuit 4 counts the number of the particles fed from the gate circuit 3. A memory 5 is connected to the counter circuit 4. The detector 1 is additionally connected to the arithmetic circuit 6, to which the memory 5 is connected. The reference numeral 7 designates a controller circuit which is connected to the gate circuit 3, the counter circuit 4 and the memory 5. The arithmetic circuit 6 is connected to a display 8 and/or a recorder 9. The reference numerals 11 and 12 designate a reference voltage generator and a reference pulse generator, respectively.

Figure 2:
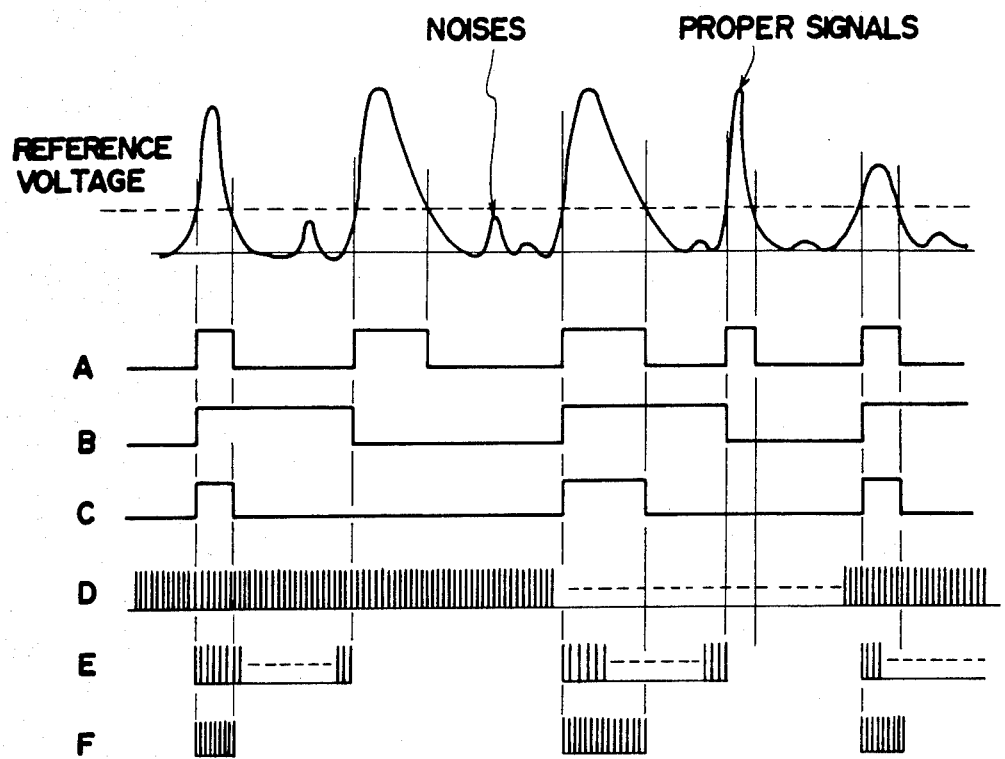
FIG. 2 is explanatory charts showing various waveforms of the pulses.

An output from the detector 1 is amplified by the amplifier 10. The detected signals are represented in a graph on top in FIG. 2, from which unnecessary components like fragmental signals or noises are removed by the threshold circuit 2 across which the reference voltage is impressed by the reference voltage generator 11. As a result, Signal (A) (FIG. 2) is obtained. By operating a flip-flop at the rising points of the pulses, the Signal (B) is obtained. Signal (C) is obtained by taking the elements in common (AND) with both Signals (A) and (B). Signals (B) and (C) are generated as gate signals at the gate circuit 3, wherein Signal (B) represents the intervals of detecting particles while Signal (C) representing the widths of the detecting pulses. The gate circuit 3 receives the reference pulse signal (D) from the reference pulse generator 12, and transmits a series of signals to the counter circuit 4 for a predetermined period of time. In FIG. 2 Signal (E) represents the pulse intervals, and Signal (F) represents the pulse widths. Signals (E) and (F) are separately counted by the counter circuit 4. Each of the counted values is used to operate the controller circuit 7 at the descending points of Signals (B) and (C), and is stored directly in the memory 6, wherein the arithmetic circuit 6 is not employed. More concretely, the numbers stored at the address corresponding to the counted value at the counter circuit 4 are read out, and 1 is added to the number; then, it is again stored at the same address. Each of the counted values for Signals (E) and (F) is treated in this way. When necessary, the counter circuit 4 is reset to zero after a sufficient time has held for writing in the memory 5. The afore-mentioned operation is commonly called a direct memory access (DMA), which is characterized by the non-use of the arithmetic circuit 6. This operation has an advantage that the required time can be shortened to a few microseconds or less.

When the amount of the particles to be detected is predetermined, a controller in the detector 1 is used to generate signals for initiating arithmetic operation, and a timer incorporated in the arithmetic circuit 6 is used to generate signals for stopping the detection after a predetermined period of time has passed. The former signals also initiate the subsequent operation of the arithmetic circuit 6, and the latter signal is also used to stop introducing the medium into the pore as well as to initiate the arithmetic operation. In FIG. 2 Signals (B) and (C) show that the measurement has been carried out on each other particle, but the embodiment is not limited to this method. By adding further units of the gate circuit 3 and the counter circuit 4 so as to count alternately, a continuous measurement is made possible, which advantageously doubles the amount of information. More concretely, a reversed signal (B') is taken from Signal (B), and as mentioned above, the portions in common (AND) with Signals (A) and (B') are taken to make Signal (C'). By gating the gate circuit 3 with these Signals (B') and (C'), Signals (E') and (F') are generated to make up for the intervals between Signals (E) and (F).

Figure 3:
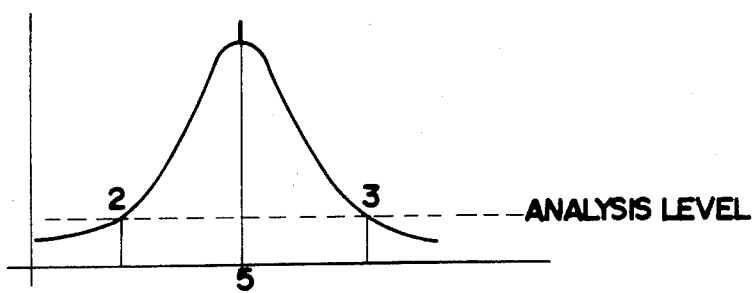
FIG. 3 shows one example of the graphs for displaying or recording.

The arithmetic circuit 6 reads out the numbers directly stored at the individual addresses in the memory 5, and the read-out data are represented in a graph for recording or displaying at 8 or 9. An example of the graphs obtained is shown in FIG. 3, and at the same time the following items are also calculated, which are printed:

1. Peak value: X-axis value,
2. Minimum: X-axis value,
3. Maximum: X-axis value,
4. Width: 3 to 2,
5. Mean: X-axis value which amounts to ½ in area above the analysis level,
6. Height: Y-axis value corresponding to the peak value,
7. Counter: Count number at the count level.

Figure 4:
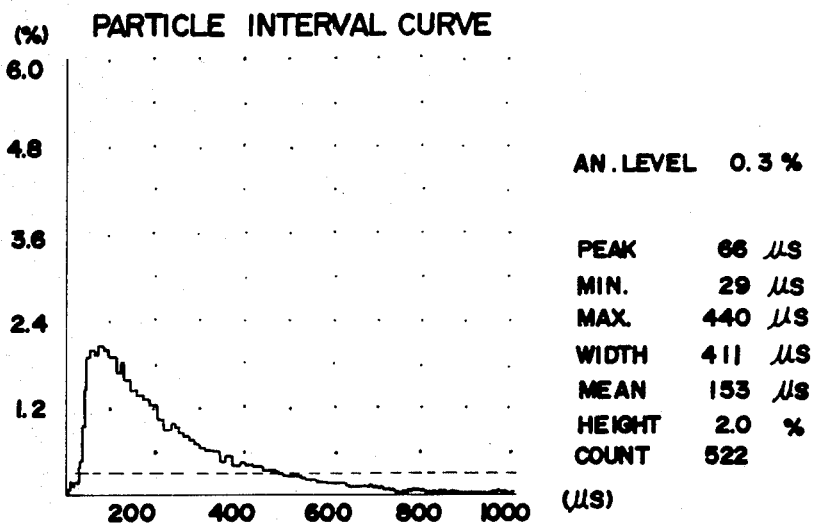
FIGS. 4 to 6 show graphs represented in a printed form.
Figure 5:
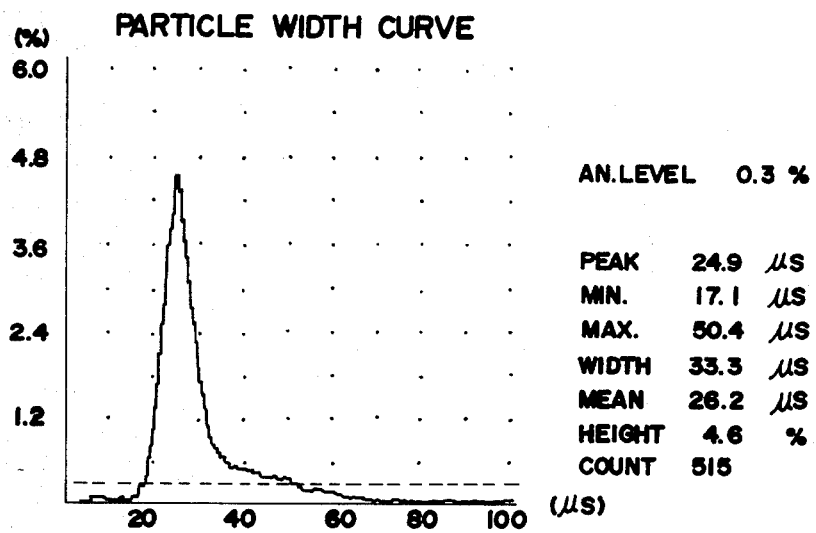

FIGS. 4 and 5 show actual examples of representation in a printed form, wherein the specimen was blood. FIG. 4 shows a graph for particle intervals and data obtained from the arithmetic operation. The mean value of particle intervals is 153 microseconds. FIG. 5 shows a graph for the widths of pulses with respect to a blood from a different person, from which it will be understood that the mean value is 26.2 microseconds and that the peak value is 24.9 microseconds. As evident from FIGS. 4 and 5, it will be understood that it is essential to pass the dispersion medium through the pore at a constant speed. If any clogging or variation occurs in the course of passing the medium, the resulting graph will fail to obtain the peak or at least the clear-cut peak, and the results of arithmetic operation will become unstable. When the analyzer of the invention is employed, these faulty results will be readily observed and called to the inspector's attention. Therefore, the analyzer can be used as a checker for such situations. For example, it is used to examine the accuracy of a blood corpuscle counter and a blood platelet counter now in wide use in the clinical inspection. It will make it possible to previously know not only a daily rate of variations but also a possible occurence of noises, possible variations of pulse widths due to the varying responsibility of the apparatus, or any other variations in the measuring conditions.

Figure 6:
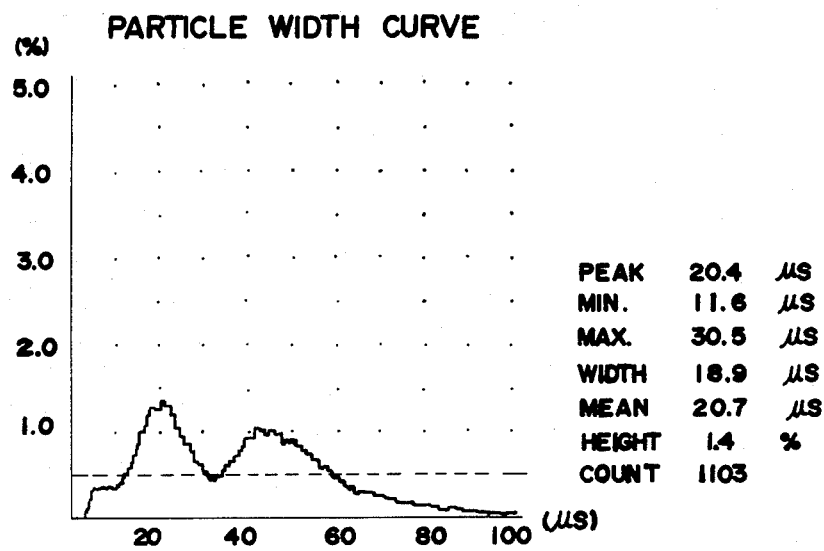

With the use of the analyzer of this invention it is possible to examine the characteristic of a dispersion medium which contains particles of different sizes—large and small. FIG. 6 shows the results obtained a situation in which the medium contains an equal amount of large particles and small particles. The resulting graph is characterized by two peaks in which the analysis level is drawn passing through the bottom of the valley between the two peaks. By calculating the areas of each mountain above the analysis level, it is possible to inspect the particle size ratios and/or the number of particles per unit volume. To simultaneously count the numbers of erthrocytes and blood platelets in a blood, the common practice is to deduce each figure from different heights of the detected pulses, but this measuring method presupposes a single information, which is not sufficient for achieving full data. Consequently, some statistical remedying operations will be required. In contrast, under the present invention the measurement is carried out on the basis of time for which dispersion medium is passed through the detection pore, which constitutes quite a different parameter. If the values obtained from the pulse heights in the known manner are compensated for by those obtained under the present invention, the measurement will be made more accurate and reliable.

It frequently happens that the particles dispersed in the medium become aggregate for some reason or other, so that agglomerations of particles occur. This will enlarge the pulse intervals. On the other hand, the particles are also subjected to reduction in the ambient pressure, and make their loose linkage. Under such circumstances the particles tend to scatter immediately before the detection pulses are generated, which results in uneven pulse intervals. The resulting curve for the pulse interval becomes horizontally lengthwise, and probably will have two peaks. In such a situation, the analyzer of the invention can carry out the analyzing without losing its efficiency.

In clinical examinations it often happens that the testing erthrocytes become agglomerated due to the low temperature. Such agglomerations are well observed at 0° C. to 5° C., but they are disappearing at 20° C. to 30° C. At 37° C. or more they are no longer observed. According to the invention, the reduction in pulse intervals due to the increase in temperature is well observed and analyzed.

What is claimed is:

1. A particle size distribution analyzer adapted for observing the health conditions of particles, such as blood cells, the analyzer comprising a detector adapted to detect particles by electrical or optical differences from a medium containing the particles in dispersion and generate signals proportionally to the size of the detected particles, a threshold circuit adapted to remove noises or fragmental signals from the detected signals so as to obtain threshold circuit pulse widths at a constant position, a gate circuit for generating a gate circuit pulse interval signal and a gate circuit pulse width signal from the threshold circuit pulse widths, a counter circuit adapted to count the gate circuit pulse interval signal and the gate circuit pulse width signal from the gate circuit, a memory connected to the counter circuit for storing data, an arithmetic circuit connected to the memory for reading out the data stored in the memory and connected to the detector for stopping the detector after a predetermined lapse of time, a controller circuit connected to the gate circuit, the memory and the counter circuit for controlling the gate circuit, the memory and the counter circuit, and means for displaying or recording the data read out by the arithmetic circuit.

* * * * *